United States Patent [19]

Schlapfer et al.

[11] Patent Number: 5,501,684

[45] Date of Patent: Mar. 26, 1996

[54] OSTEOSYNTHETIC FIXATION DEVICE

[75] Inventors: Johannes F. Schlapfer, Glarus; Martin Hess, Holstein, both of Switzerland

[73] Assignee: Synthes (U.S.A.), Paoli, Pa.

[21] Appl. No.: 199,130

[22] PCT Filed: Jun. 25, 1992

[86] PCT No.: PCT/CH92/00125

§ 371 Date: Jul. 26, 1994

§ 102(e) Date: Jul. 26, 1994

[87] PCT Pub. No.: WO/9400066

PCT Pub. Date: Jan. 6, 1994

[51] Int. Cl.⁶ .................................................. A61B 19/84
[52] U.S. Cl. ........................... 606/73; 606/72; 606/61; 606/69; 403/90
[58] Field of Search ...................... 606/69, 70, 71, 606/61, 60, 59, 54–58, 72, 73, 76, 104, 151, 157; 623/16, 17; 403/90, 87, 131, 84

[56] References Cited

U.S. PATENT DOCUMENTS

| 4,422,451 | 12/1983 | Kalamchi | 606/61 X |
|---|---|---|---|
| 4,484,570 | 11/1984 | Sutter et al. | 606/71 X |
| 4,836,196 | 6/1989 | Park et al. | 606/61 X |
| 4,905,680 | 5/1990 | Tunc | 606/69 |
| 5,002,542 | 3/1991 | Frigg | 606/61 |
| 5,047,029 | 9/1991 | Aebi et al. | 606/61 |
| 5,053,036 | 10/1991 | Perren et al. | 606/69 |
| 5,057,111 | 10/1991 | Park | 606/69 |
| 5,129,899 | 7/1992 | Small et al. | 606/61 |
| 5,261,910 | 11/1993 | Warden et al. | 606/61 |

FOREIGN PATENT DOCUMENTS

| 0216563 | 4/1987 | European Pat. Off. . | |
| 0450075 | 10/1991 | European Pat. Off. . | |
| 2640493 | 6/1990 | France . | |
| 2933637 | 4/1980 | Germany | 606/70 |
| 3027138 | 12/1981 | Germany . | |
| 8609102 | 4/1987 | Germany . | |
| 8803781 | 6/1988 | WIPO . | |

*Primary Examiner*—Stephen C. Pellegrino
*Assistant Examiner*—Guy V. Tucker
*Attorney, Agent, or Firm*—Fish & Richardson

[57] ABSTRACT

An osteosynthetic fixation device consists of a fixation element 1 which has a conical head section 11 and an anchoring element 12 abutting it which is for attachment into the bone. The fixation device also consists of a spherically formed, layered, slotted clamping piece 2 which has a conical borehole 21 for installation of the conical head section 11, and which is meant for locking within a connecting piece 3 equipped with a spherically shaped layered borehole 31. Fixation piece 1 has an axially arrayed tension element 4, permitting axial displacement and wedging of conical head section 11 in the borehole 21 that corresponds with it. The fixation device is appropriate for use as a plate/screw system, an internal or external fixator, and in particular for spinal column fixation.

25 Claims, 3 Drawing Sheets

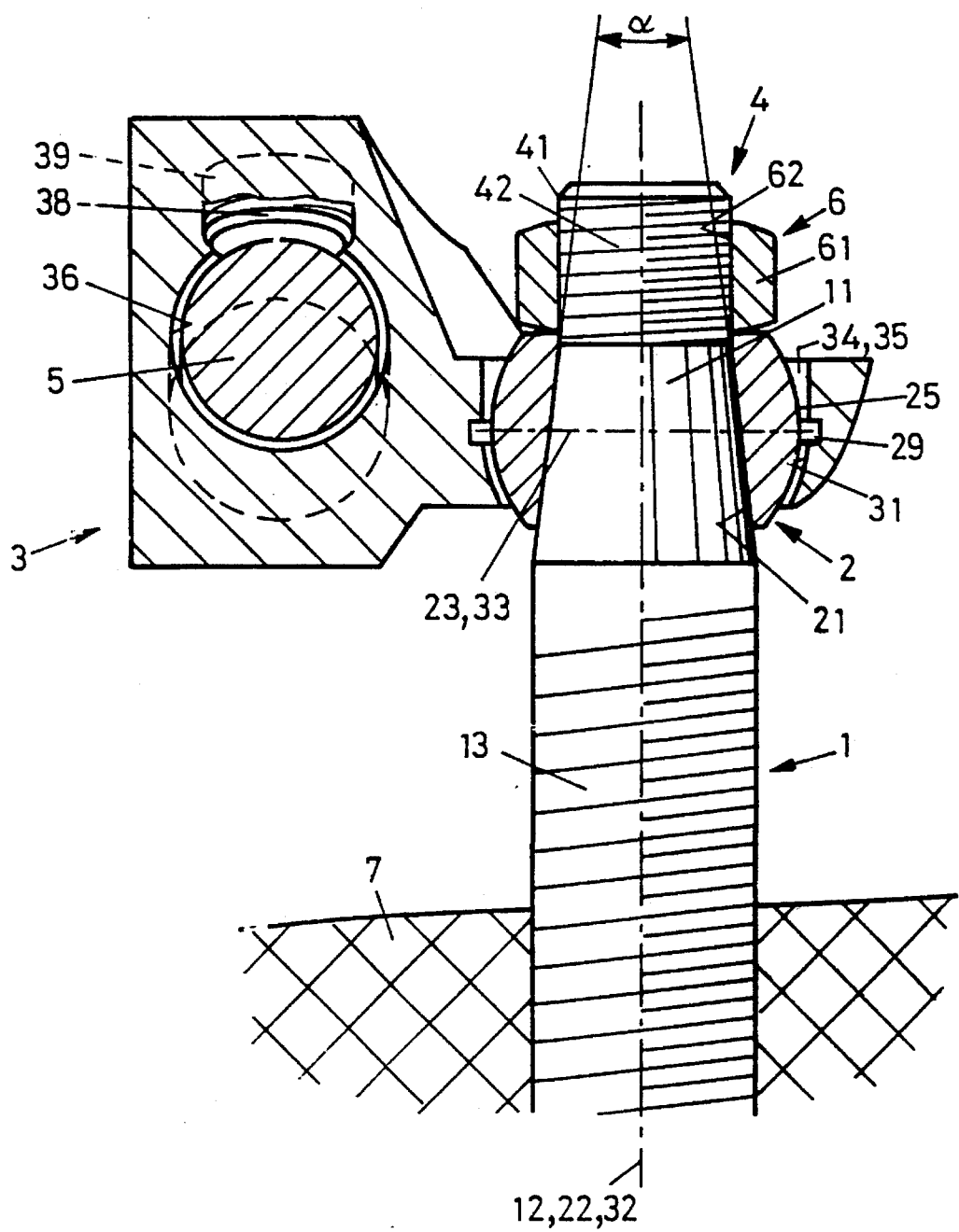

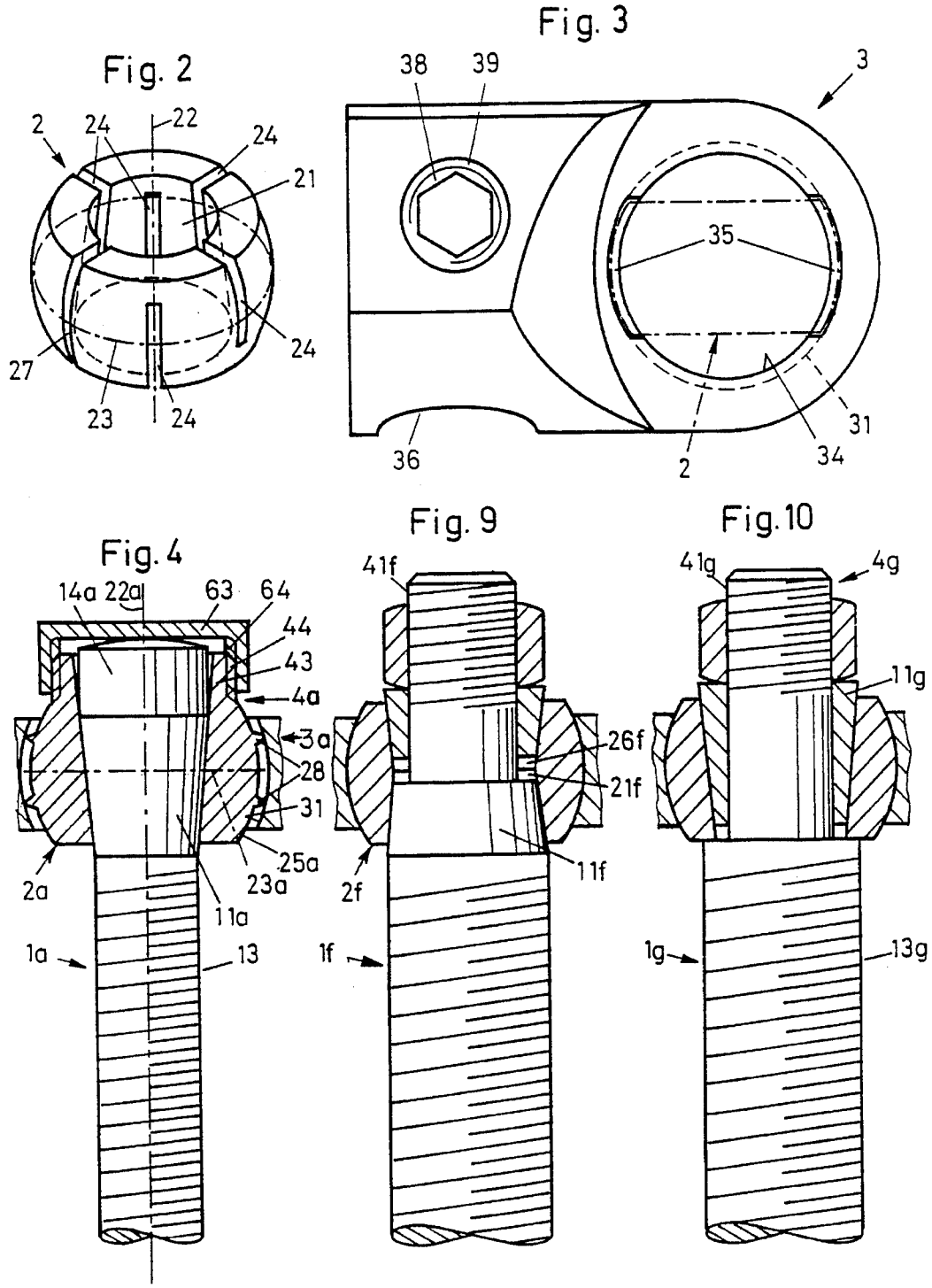

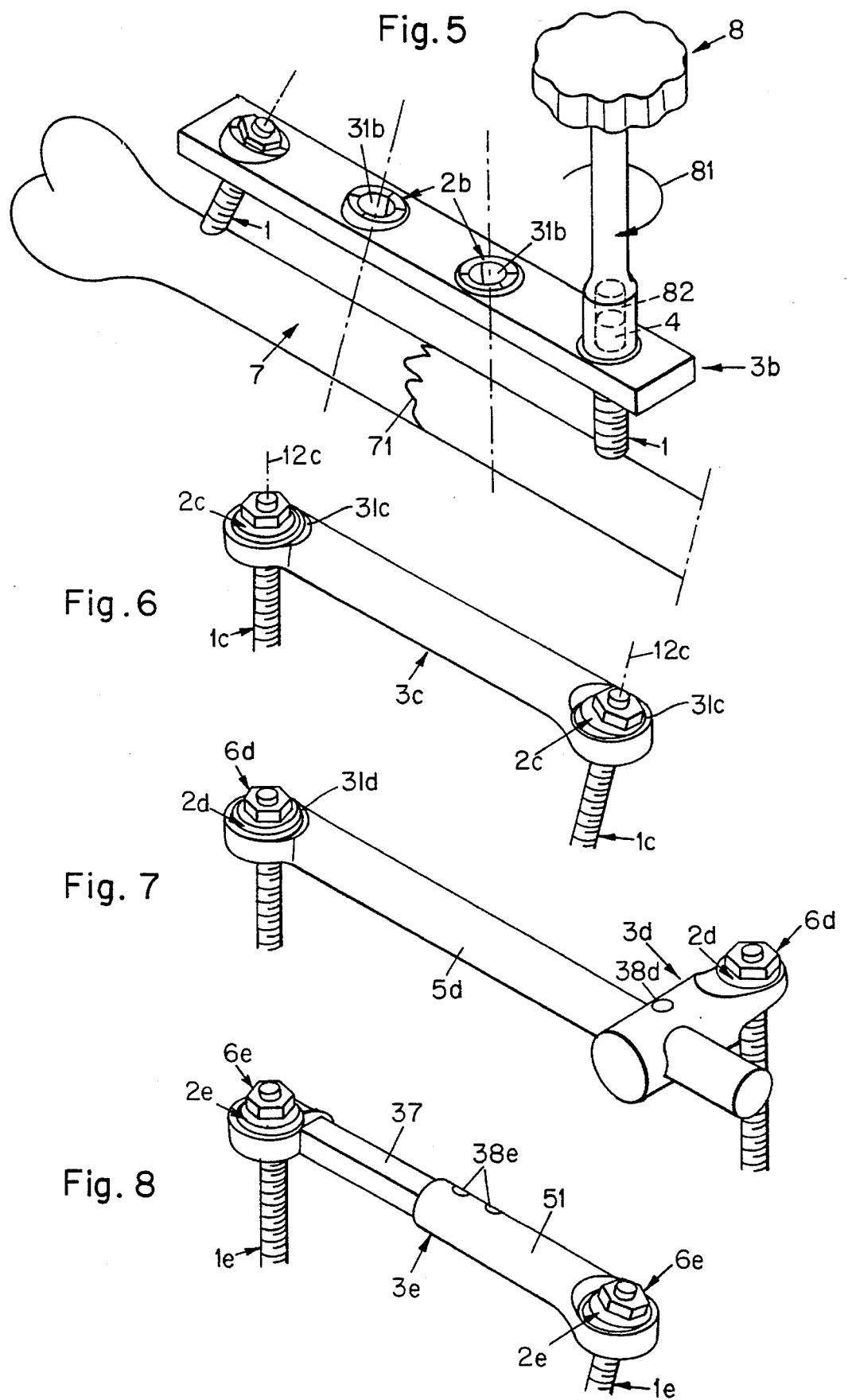

OSTEOSYNTHETIC FIXATION DEVICE

FIELD OF THE INVENTION

The invention relates to an osteosynthetic fixation device.

BACKGROUND OF THE INVENTION

In osteosynthesis there are a multitude of requirements for reciprocal fixation of the involved bone fragments. For this reason, a great number of fixation devices are already known, such as plate/screw systems, external fixators, internal fixators, spinal column fixation systems, etc.

Many of these known devices permit working only in two dimensions, which severely limits their applicability. A further disadvantage is the lack of ability, or only limited ability, to adapt the fixation device during the operation, i.e. to loosen the connection between the individual fixation parts easily and quickly and then lock them to each other in another relative position.

From DE-A-30 27 148, a bone plate, for example, with a hemispherical-shaped screw hole opening upwards, into which a spherical, slotted clamping piece with a conical borehole can be inserted, is known. Through the conical borehole of the clamping piece seated in the plate, a bone screw with a matching conical head can be screwed into the bone, until the conical screw head comes into contact in the conical inner borehole with the clamping piece. It expands the clamping piece and locks it within the screw hole of the plate.

The disadvantage of this known device is that the bone screw is not rigidly attached to the bone plate. As soon as the screw loses its attachment in the bone material, it can easily become loosened from the clamping piece or from the plate. This known anchoring concept can therefore be used only on bone plates. This concept cannot be applied to an external fixator or to a spinal column fixation system, because a rigid attachment between the individual parts is lacking; the fixation is maintained temporarily, only as long as the bone screw is securely seated in the bone material, and the bone plate presses against the bone.

From EP-A2 355 035 another bone plate is known, in which, similar to DE-A 30 27 148, the screw hole is equipped with an inner wall formed of spherical segments, which here, however, extends on both sides of a great circle, i.e., it narrows down against both sides of the plate from a line of maximum girth or circumference. The document goes on to disclose an automatic locking of the component parts. However, the following are disadvantages of this known device:

- The locking of the screw in the clamping piece is done by rotation at the same time it is screwed into the bone using a hex wrench. While this is going on, there is a rapid onset of friction forces between the conical adjoining surfaces of both parts, which hinders screwing in of the bone screw.
- The screw can be set into the bone only after the complete positioning of the bone plate. Attachment of an already implanted screw to the plate or to another part acting as an attachment piece is not possible.
- The concept only works as long as the plate securely lies upon the bone and the bone exhibits good anchoring properties. As soon as the plate ceases to contact the bone, the attachment no longer functions.

In this regard the invention will constitute a remedy. The purpose of the invention is to create an osteosynthetic fixation device that is adjustable in three dimensions, and permits the individual parts easily and quickly to be locked in rigid fashion to each other, and also unlocked.

SUMMARY OF THE INVENTION

The invention solves the problem presented with an osteosynthetic device having the characteristics mentioned in claim 1.

Additional advantageous configurations of the invention are characterized in the appended claims.

The general locking concept of the invention-specific fixation device is described below.

Depending on the configuration of the invention, the actual fixation piece or element to be anchored in or on the bone is either admitted into the conical borehole of the spherically formed clamping element seated in the connecting element, or else the latter is slid over the conical head section of the fixation device. The connecting element for its part can be connected with a longitudinal outrigger. Then an appropriate instrument is used to adjust the angle between the connecting element (or the longitudinal outrigger inserted in it) and the fixation element (for example, for repositioning a vertebral fracture), and to lock the cone at the same time. The angle referred to can be adjusted in all directions (i.e., three-dimensionally), by sliding the instrument back and forth like a control lever. By turning the instrument clockwise, the fixation element is increasingly driven into the clamping element. Thereby, the latter is spread and locked with simultaneous locking of the cone.

Thus in this procedure the instrument acts as a nut in which the tension piece of the fixation device, acting as a screw, is screwed in and driven relative to the longitudinal axis. Hence, wedging of the fixation element in the clamping element is done not by rotary motion, but rather solely by an axial displacement of the two pieces against each other.

In one preferred embodiment, the cone is designed to lock automatically, by having a conical half angle of about 4° for the head section of the cone and the conical borehole in the clamping element. Automatic locking has an advantage in that the connection created between the component parts after removal of the instrument will not be broken apart. Depending on the configuration, either a nut or a screw cap with an interior threading will be used to secure the device. The nut or screw cap is not normally used to draw the fixation element into the conical borehole or to draw the clamping element over the cone of the fixation element. Where there is a very oblique conical angle, the nut or screw cap can also be dispensed with as a securing element.

The clamping element can either be seated firmly, but capable of being turned, in the borehole of the connecting element, or else be detachable by means of a suitable refinement. For this purpose, the borehole of the connecting element is provided in one of its two openings with two recesses arranged so that they are offset by 180°. This permits the clamping element to be inserted and removed without applying force, in that it can be turned by 90° and pressed outward from its seat.

Preferably the conical head section of the fixation element will taper down in the direction of its free end, the end which is remote from the anchoring piece, since this facilitates subsequent attachment of the connecting element from beneath, or allows it to take place. However, a reversed cone is also possible, which must be inserted into the connecting element from above.

The conical head section is appropriately connected as a single piece with the anchoring section; however, it can also be configured as a separate piece, as a hollow pin, for example.

The slits which run transverse to the great circle of the clamping element and cause it to be expandable are preferably configured so as to alternate, some from above and some from below, preferably with one of them running all the way through. Another option is to provide the clamping element with slits only on the side of the greatest diameter of its conical borehole.

It has further been shown that roughening the spherical-zone-forming surface of the clamping element and/or the spherical inner surface of the connecting element (e.g., by corundum blasting) is appropriate or this can be done by structural design (e.g., by creating a sharp-edged groove on the spherical inner surface of the connecting element, combined with a clamping element made of a softer material). Another version consists of redesigning the spherical surface of the clamping element, such as with sharp edges and combining with a connecting element made of a relatively soft material.

The connecting element is preferably provided with a circular cylindrical channel into which a longitudinal outrigger can be admitted. This, for example, allows use of the device according to the invention in the spinal column area. For special applications, such as in the sacral area, the channel can exhibit an inclination (such as 25°) relative to the horizontal plane of the connecting piece that here forms the sacral bucca.

The tension element according to the invention is preferably configured as a circular cylinder section aligned axially with the head section of the fixation element. The section has exterior threading.

However, it is also possible to configure the tension element as a circular cylinder section aligned axially with the clamping element, also with exterior threading.

With the clamping concept according to the invention, it is also possible to join multiple fixation parts such as bone screws, one beneath the other. In addition, design as a one-sided, two-sided or adjustable external or internal fixator is possible.

The advantages obtained through the invention can essentially be said to consist of the following: that thanks to the fixation device according to the invention, an overall low device height is attained; three-dimensional adaptability is ensured; repositioning of bone fractures and locking of the fixation device take place simultaneously in a single tension; clamping is generated by a pure translational motion of the clamping piece relative to the fixation piece; and, by means of a suitable pairing of materials between the clamping piece and the fixation piece, friction between the two components is kept to a minimum.

DESCRIPTION OF THE DRAWINGS

The invention and further refinements of the invention will be given in greater detail below with the aid of partially schematic drawings of numerous configurational examples.

In the drawings:

FIG. 1 is an axial cross section of the device according to the invention.

FIG. 2 is a perspective view of the clamping piece according to FIG. 1.

FIG. 3 is a view from below of the connecting piece according to FIG. 1.

FIG. 4 is a partial axial cross section of a modified version of the invention.

FIG. 5 is a perspective view of a bone plate with several fixation and clamping pieces.

FIG. 6 is a perspective view of a fixation device according to the invention serving as a two-sided internal fixation device.

FIG. 7 is a perspective view of a fixation device according to the invention serving as a one-sided internal fixation device.

FIG. 8 is a perspective view of a fixation device according to the invention serving as a longitudinally-adjustable internal fixator.

FIG. 9 is an axial cross section of a further modified configuration of the invention.

FIG. 10 is an axial cross section of a further modified configuration of the invention.

DESCRIPTION OF PREFERRED EMBODIMENT

The fixation device depicted in FIG. 1 is meant for insertion of an implant in the sacral area. Essentially it consists of a fixation piece or element 1 (here formed as a pedicle screw), a clamping piece or element 2 which is seated in connecting piece or element 3, and securing piece or element 6.

The pedicle screw has a conical head section 11 and an anchoring element 13 (here formed as a threaded shaft) adjoining the head section for fastening into bone 7. In addition, the pedicle screw has a circular cylinder section 41 with an exterior threading 42, arranged along its longitudinal axis 12. This serves as a tension element 4 and permits displacement and wedging of conical head section 11 relative to clamping element 2. Conical head section 11 tapers down in the direction of its free end which faces away from the threaded shaft at a conical angle $\alpha/2$ of about 4°.

Clamping element 2 depicted in detail in FIG. 2 has a conical borehole 21 for form-locking and force-locking installation of conical head section 11 of the pedicle screw. Its configuration is that of a spherical shell, and it extends to both sides of a great circle 23, i.e. a circumferential line encircling the clamping piece at its maximum girth. Its longitudinal axis 22 coincides with longitudinal axis 12 of the pedicle screw as shown in FIG. 1. Since, however, the two parts 1, 2 prior to being reciprocally locked are arranged to be able to be turned against each other, the two longitudinal axes 12, 22 may deviate from each other over a wide range. Clamping element 2 is provided with slits 24 running transverse to great circle 23; these are arranged to run alternately from above and below. One such slit 27 is configured to run fully through. In one version which is not depicted, the slits 24 run only from the side of the larger diameter of conical borehole 21 to great circle 23.

Connecting element 3 formed in this configuration as a sacral bucca exhibits a spherically formed borehole 31 for form-locking installation of spherically formed clamping element 2. Longitudinal axis 32 of borehole 31 coincides in FIG. 1 with axes 12, 22. The surface of borehole 31 extends on both sides of great circle 33, so that clamping element 2 is securely embedded into it and there is no possibility of it being knocked out in an axial direction 12, 22, 32 from below or above. Spherical borehole 31 also has a sharp-edged groove 29; this results in improved locking, particularly if clamping piece 2 consists of a softer material than fixation element 1.

As FIG. 3 depicts, spherical borehole 31 of connecting piece 3 formed as a sacral bucca is equipped in its lower openings 34 with two recesses 35 which are configured to be offset by 180°, permitting insertion and removal of clamping element 2. For this purpose, clamping element 2 is turned 90° so that its longitudinal axis 22 is perpendicular to longitudinal axis 32 of borehole 31, and its contact surface is aligned to the recesses 35. Clamping element 2 can then be removed from borehole 31 without applying force.

Locking of the fixation device according to the invention is done by use of an instrument 8 depicted in FIG. 5, which has an interior thread 82 in its front end. By turning clockwise, the exterior thread 42 of tension element 4 is screwed into interior thread 82, until instrument 8 hits clamping element 2, and thereby fixation element 1 is drawn axially into conical borehole 21. This causes clamping element 2 to be expanded, thanks to its slits 24, and locked into borehole 31. The surface 25 of spherically formed clamping piece 2 or the spherical inner surface of connecting piece 3 is appropriately roughened, or possesses a structural design to attain an optimal locking into borehole 31.

At the same time, of course, the two elements 1, 2 are locked against each other along their conical surfaces. The conical angles $\alpha/2$, i.e. of conical head section 11 and conical borehole 21, both are 2°–7°, preferably 3°–5°. With a conical angle $\alpha/2$ of this size, an optimal automatic locking and fixation of the two elements 1 and 2 against each other is effected.

Connection piece 3, formed as a sacral bucca, is in addition provided with a circular cylindrical channel 36 (FIG. 1), which forms an angle of 25° relative to the horizontal plane (as it is defined by great circle 33). A longitudinal outrigger 5 is placed in channel 36, which can be fixed in any position whatever by means of set-screw 38 in a borehole 39 which leads to channel 36.

After locking of the individual parts is accomplished, a nut 61 acting as a fastening element 6 with an interior threading 62 corresponding to exterior threading 42 of tension element 4, is screwed onto circular cylinder section 43.

FIG. 4 depicts a version of the fixation device according to the invention in which tension element 4a is not attached to fixation element 1a, but rather axially to clamping element 2a. Tension element 4a here consists of a circular cylindrical section aligned with longitudinal axis 22 of clamping element 2a. The circular cylindrical section has an external thread 44. The conical head section 11a of fixation piece 1a here has an extension 14a in circular cylindrical form.

Reciprocal locking of pieces 1a, 2a can be done by means of the same instrument 8 (FIG. 5), in fact, with a relatively short interior thread 82. By turning instrument 8 clockwise, exterior thread 44 is again turned into interior thread 82 until instrument 8 hits extension 14a, and thus the same procedures are followed as with the design configuration of FIGS. 1–3.

To improve fixation, the spherically shaped surface 25a of clamping element 2a has sharp edges 28 running parallel to great circle 23a, and the connecting element 3a in this design configuration is made of a softer material than clamping element 2a.

After locking of the separate elements is done, a cap 63 which serves as a securing element and has an interior thread 64 corresponding to exterior thread 44, is screwed onto circular cylinder section 43.

As depicted in FIG. 5, connecting element 3b of the fixation device according to the invention can also be formed as a bone plate. In the four spherically shaped layered boreholes 31b, four clamping elements 2b are fitted, into which, if need arises, bone screws in the form of fixation piece 1 according to FIG. 1 can be fastened.

FIG. 6 depicts a fixation device according to the invention in the form of a two-sided internal fixator with a set length. Both ends of connecting element 3c exhibit a spherically shaped layered borehole 31c with a clamping element 2c fitted in, into which fixation element 1c can be inserted and locked in place. The position of longitudinal axis 12c in both fixation elements 1c, thanks to the spherical clamping element 2c, is adjustable over a wide angular range.

FIG. 7 depicts a fixation device according to the invention in the form of a one-sided internal fixator, which consists of longitudinal outrigger 5d with a single spherically shaped borehole 31d made on its left side, with a clamping element 2d fitted in. On the right end of longitudinal outrigger 5d, a connecting element 3d analogous to the sacral bucca in accord with FIG. 1 has been mounted onto longitudinal outrigger 5d and fixed in detachable fashion onto it by means of set-screw 38d, so that it can be slid at will back and forth. Nuts 6d are again provided to secure the fixation.

FIG. 8 depicts a fixation device according to the invention in the form of a universal, longitudinally adjustable internal fixator. It consists of a connecting element 3d analogous to the sacral bucca according to FIG. 1, with a square segment 37 and a with a hollow segment 51 possessing a square-cut interior. The square segment 37 can thus be longitudinally inserted into hollow segment 51 and fixed in any position whatever by the two set-screws 38e. Both segments of connecting element 3e exhibit a spherically shaped borehole 31e with clamping element 2e fitted in, in each of which a fixation element 1e can be inserted, locked and secured by means of nut 6e.

Instead of a square cross section for the two telescoping segments 37 and 51, any polygonal or circular cross section can be chosen. With a circular cross section, the surface of pieces 37 and 51 should preferentially be longitudinally splined, to obtain a joint which is rotationally stable.

FIG. 9 shows an additional version of a fixation device according to the invention. In it the conical head section 11f of fixation piece 1f, which is formed as a bone screw, is dimensioned relatively short. Likewise, conical borehole 21f of clamping piece 2f which tapers up from below, extends only to a limited height of the latter, and then expands upwardly as upper conical borehole 26f. The installation of this fixation device is done essentially identically to the design of FIGS. 1–3, simply with a hollow pin 45 which corresponds to upper conical borehole 26f being slid over circular cylindrical section 41f, which locks in similar fashion with axial displacement of elements 18, 28.

Finally, FIG. 10 shows a version of the fixation device according to the invention in which conical head section 11g of fixation element 1, here formed as a bone screw, is not linked firmly with anchoring element 13g, but is formed as a separate hollow pin. This pin can be slid onto circular cylinder section 41g of tension element 4g. The locking mechanism is identical to that of the design configurations described above.

What is claimed is:

1. An osteosynthetic fixation device comprising:
   a fixation element having a longitudinal axis, a head section at least in part of conical shape and an anchoring element abutting said head section, for attachment to bone, a separate clamping element having the shape of a layer of a sphere and extending on both sides of a great circle of said sphere, said clamping element having a longitudinal axis, a conical bore hole and a plurality of slots extending transverse to said great circle and, a separate tensioning element extending from the head section for drawing and wedging the head section of said fixation element into the conical bore hole of said fixation element independent of the fixation element's attachment to the bone.

2. A fixation device according to claim 1 and comprising a connecting element having a borehole with a longitudinal axis, said borehole being shaped to seat said clamping element.

3. A fixation device according to claim 2 wherein the surface of the borehole of the connecting element extends on both sides of said great circle of said clamping element.

4. A fixation device according to claim 2 wherein the clamping element is seated within the borehole of the connecting element is to be turnable, but not removable.

5. A fixation device according to claim 2 wherein the borehole of the connecting element has two openings and at one of said openings, two recesses offset by 180°, permitting insertion and removal of the clamping element.

6. A fixation piece according to claim 2 wherein the inner surface of the borehole of the connecting element is roughened.

7. A fixation device according to claim 2 wherein the borehole of the connecting element has a sharp-edged groove, and the clamping element is made of a softer material than the fixation element.

8. A fixation device according to claim 2 wherein the surface of the clamping element has overhanging sharp edges, and the connecting element is made of a softer material than the clamping element.

9. A fixation device according to claim 2 wherein the connecting element has a channel to receive a longitudinal outrigger.

10. A fixation device according to claim 2 and comprising a plurality of fixation elements attached by a plurality of clamping elements into a plurality of boreholes each having the shape of a spherical layer in a single connecting element.

11. A fixation device according to claim 2 and comprising a plurality of fixation pieces attached by a plurality of clamping pieces into a plurality of boreholes of two connecting pieces.

12. A fixation device according to claim 1 wherein the conical head section of the fixation element tapers down in the direction of its end which is most remote from the anchoring element.

13. A fixation device according to claim 1 wherein the surface of the conical head section subtends an angle with the longitudinal axis of between about 2° and about 7°.

14. A fixation device according to claim 1 wherein the clamping element slits extend alternately from the top and bottom of said element.

15. A fixation device according to claim 14 wherein one of the slits runs continuously from top to bottom.

16. A fixation device according to claim 14 wherein the slits running transverse to great circle of the clamping element run from the edge of the larger diameter of the conical borehole to the great circle.

17. The fixation device according to claim 16 wherein one of the slits running transverse to the great circle of the clamping element runs continuously from bottom to top.

18. A fixation device according to claim 1 wherein the spherical surface of the clamping element is roughened.

19. A fixation device according to claim 1 wherein the tension element is a cylindrical segment aligned with the head section and has an exterior thread.

20. A fixation device according to claim 19 and comprising a fastening element.

21. The fixation device according to claim 20 wherein the fastening element is a nut having an internal thread corresponding to the thread of the tension element.

22. A fixation device according to claim 1 wherein the tension element is a circular cylindrical segment aligned with the clamping element and has an exterior thread.

23. A fixation device according to claim 19 and comprising a fastening element having an interior threading corresponding to the exterior threading of the tension element.

24. A fixation device according to claim 1 wherein the head section and anchoring element are formed as a single piece.

25. A fixation device according to claim 1 wherein the head section and anchoring element are formed as two pieces.

* * * * *

UNITED STATES PATENT AND TRADEMARK OFFICE
CERTIFICATE OF CORRECTION

PATENT NO. : 5,501,684
DATED : March 26, 1996
INVENTOR(S) : Johannes F. Schlapfer and Martin Hess It is certified that error appears in the above-indentified patent and that said Letters Patent is hereby corrected as shown below:

Col. 5, line 46, cancel "22" and substitute --22a--.

Col. 6, line 4, cancel "layered".

Col. 6, line 10, cancel "layered".

Col. 6, line 28, cancel "with".

Col. 6, line 53, cancel "18, 28" and substitute --1f, 2f--.

Signed and Sealed this

Twenty-seventh Day of August, 1996

Attest:

BRUCE LEHMAN

*Attesting Officer*  *Commissioner of Patents and Trademarks*